United States Patent
Ho et al.

(10) Patent No.: US 10,570,390 B2
(45) Date of Patent: Feb. 25, 2020

(54) COMPOSITIONS, DEVICES, AND METHODS FOR TREATING INFECTIONS

(76) Inventors: Rodney J. Y. Ho, Mercer Island, WA (US); Brenda Newman, Seattle, WA (US)

(*) Notice: Subject to any disclaimer, the term of this patent is extended or adjusted under 35 U.S.C. 154(b) by 571 days.

(21) Appl. No.: 14/239,516

(22) PCT Filed: Aug. 20, 2012

(86) PCT No.: PCT/US2012/051593
§ 371 (c)(1),
(2), (4) Date: May 19, 2014

(87) PCT Pub. No.: WO2013/028624
PCT Pub. Date: Feb. 28, 2013

(65) Prior Publication Data
US 2014/0255476 A1 Sep. 11, 2014

Related U.S. Application Data

(60) Provisional application No. 61/525,640, filed on Aug. 19, 2011.

(51) Int. Cl.
| | |
|---|---|
| *A61K 9/00* | (2006.01) |
| *C08B 37/00* | (2006.01) |
| *C08B 15/10* | (2006.01) |
| *C01F 11/00* | (2006.01) |
| *C12N 15/11* | (2006.01) |
| *C07K 14/435* | (2006.01) |

(52) U.S. Cl.
CPC ............ *C12N 15/11* (2013.01); *A61K 9/0014* (2013.01); *C07K 14/435* (2013.01); *C08B 15/10* (2013.01); *C08B 37/0084* (2013.01)

(58) Field of Classification Search
None
See application file for complete search history.

(56) References Cited

U.S. PATENT DOCUMENTS

| | | | |
|---|---|---|---|
| 6,592,889 B1 | 7/2003 | Stout | |
| 7,108,848 B2 | 9/2006 | Young | |
| 7,534,368 B2 | 5/2009 | Martin | |
| 7,993,545 B2 | 8/2011 | Martin | |
| 2002/0155067 A1 | 10/2002 | MacGregor | |
| 2004/0001879 A1* | 1/2004 | Guo | A61L 15/28 424/445 |
| 2006/0089584 A1* | 4/2006 | McAdams | A61F 13/2008 602/48 |
| 2006/0193789 A1 | 8/2006 | Tamarkin | |
| 2008/0008743 A1* | 1/2008 | Dedhiya | A61K 9/0056 424/443 |
| 2009/0192125 A1 | 7/2009 | Cohen | |
| 2010/0009889 A1* | 1/2010 | Smith | A01N 59/00 510/379 |
| 2010/0106103 A1* | 4/2010 | Ziebol | A61L 2/186 604/265 |
| 2011/0020474 A1* | 1/2011 | Najafi | A61K 9/0014 424/665 |
| 2012/0301556 A1* | 11/2012 | Norton | A01N 59/00 424/661 |

FOREIGN PATENT DOCUMENTS

| | | | | |
|---|---|---|---|---|
| WO | 92/09291 A1 | 6/1992 | | |
| WO | 95/09607 A1 | 4/1995 | | |
| WO | 99/65538 A1 | 12/1999 | | |
| WO | WO 0238097 A1 * | 5/2002 | ......... | A61F 13/0203 |
| WO | 20061074455 A2 | 7/2006 | | |
| WO | 20061088790 A2 | 8/2006 | | |
| WO | 20101012824 A1 | 2/2010 | | |
| WO | WO-2011062707 A1 * | 5/2011 | ........... | A61K 6/0035 |

OTHER PUBLICATIONS

J.F. Siqueira Jr. et al., "Fungi in endodontic infections," Oral Surgery Oral Medicine Oral Pathogology, vol. 97, No. 5, 2004, pp. 632-641.*
International Search Report and Written Opinion dated Dec. 12, 2012, issued in corresponding International Application No. PCT/US2012/051593, filed Aug. 20, 2012, 13 pages.
Wang, L., et al., "Hypochlorous Acid as a Potential Wound Care Agent: Part I. Stabilized Hypochlorous Acid: A Component of the Inorganic Armamentarium of Innate Immunity," Journal of Burns and Wounds 6:65-79, published online Apr. 11, 2007.

* cited by examiner

*Primary Examiner* — Monica A Shin
(74) *Attorney, Agent, or Firm* — Kyaw Tin

(57) ABSTRACT

Compositions, devices, and methods for treating infections.

12 Claims, 13 Drawing Sheets

*20 hrs.*

*Fig. 8A.*

*20 hrs*

*Fig. 8B.*

92 hrs

*Fig. 8C.*

92 hrs

*Fig. 8D.*

16 hrs

*Fig. 9A.*

40 hrs

*Fig. 9B.*

*No Rinse*
*Fig. 10A.*

*w/Rinse*

16 hrs

*Fig. 11A.*

16 hrs

*40 hrs*

*Fig. 11D.* w/o Alginate

*Fig. 12A.* with Alginate to form gel

COMPOSITIONS, DEVICES, AND METHODS FOR TREATING INFECTIONS

CROSS-REFERENCE TO RELATED APPLICATION

This application claims the benefit of U.S. patent application Ser. No. 61/525,640, filed Aug. 19, 2011, expressly incorporated herein by reference in its entirety.

BACKGROUND OF THE INVENTION

Superficial (skin, hair, and nail) fungal and bacterial infections are estimated to affect over 1 billion people worldwide and 27 million people in the US. Superficial fungal infection of the skin and nails is common and is on the rise due to an aging population, the increasing prevalence of diabetes, and the widespread use of antifungals and antibiotics in medicine and in the environment. In diabetics and the immunosuppressed, onychomycosis is a risk factor for serious infections, such as cellulitis and foot ulcers. For some, however, nail infection is simply a cosmetic issue.

Fungal infection of the nail, known as onychomycosis, is a common and difficult to treat condition, most frequently affecting the toes. Dermatophyte molds (e.g., *Trichophyton rubrum*) cause the majority of infected nails, followed by yeasts, such as *Candida albicans*, and the non-dermatophyte molds, such as *aspergillus*. Infection usually starts in the skin, (so-called "athlete's foot"), and then spreads to the nail unit after trauma breaks the seal between the nail plate and the nail bed, allowing fungi to penetrate the nail. Fungi are typically found in the nail plate itself and below the nail plate in the nail bed.

Commercially available treatments include systemic administration of antifungal compounds such as griseofulvin, ketoconazole, itraconazole, fluconazole, and terbinafine. Systemic therapies, while more effective, carry the risk of serious side effects including liver failure, severe allergic reactions, as well as drug interactions. Furthermore, systemic therapies often require long-term treatment courses and laboratory monitoring.

Topical application of an antifungal drug is an attractive alternative to systemic administration. However, most topical antifungal formulations (e.g., clotrimazole, terbinafine) are totally ineffective for onychomycosis because they do not penetrate the nail, likely due to their high molecular weight. There are two topical antibiotics currently being marketed for onychomycosis: ciclopirox and amorolfin. Unfortunately, however, they not been very effective with cure rates in the 5-30% range. Thus, there is a need for an effective, safe, and convenient treatment for onychomycosis.

Halogen-based compounds have been used for treatment of infections including onychomycosis. Halogen based formulations readily penetrate the nail because of their small molecular weight. However, currently available halogen solutions (e.g., Dakin's solution) are unstable once applied to the nail, limiting their use. Furthermore, efficacy and side effects of topically applied halogen based solutions have not been well studied in the clinical setting. Sodium hypochlorite, available commonly as bleach, is a known skin irritant. Furthermore, it is well known that the chlorine, chlorine dioxide, and hypochlorous acid decompose readily upon exposure to light and air. The use of a chlorine dioxide solution as an antimicrobial agent is described in WO 2006/088790. In this study, subjects were required to soak the whole foot in a large volume of freshly made chlorine dioxide solution while in a darkened room. Aside from the inconvenience, the normal skin and nails are unnecessarily exposed to chlorine dioxide potentially causing irritation. Furthermore, high concentrations of chorine dioxide can constitute an explosive hazard.

Despite the advances in the treatment of infections, particularly skin and skin appendage infections, a need exists for a simple and effective treatment that do not suffer from the disadvantages noted above. The present invention seeks to fulfill this need and provides further related advantages.

SUMMARY OF THE INVENTION

In one aspect, the invention provides a composition, comprising a polymer crosslinked with a multivalent metal ion and a hypohalite coordinated to the metal ion. In one embodiment, the polymer is a carboxylic acid-containing polymer (e.g., an alginate or a carboxylalkylcellulose). In certain embodiments, the multivalent metal ion is a divalent metal ion, a trivalent metal ion, or mixtures thereof. Representative divalent metal ions include magnesium, calcium, strontium, and barium ions. Suitable hypohalites include hypofluorites, hypochlorites, hypobromites, and hypoiodites. The composition can be in the form of a hydrogel, dry powder, liquid solution or microencapsulated particle.

In another aspect of the invention, methods for treating a viral, bacterial, fungal, or parasitic infection are provided. In one embodiment, the method includes contacting a site of infection with a therapeutically effective amount of a composition of the invention. The method is effective for treating sites of infection including skin and skin appendages (e.g., nail) and mucosa.

In a further aspect, the invention provides a method for topical application of a hypohalite. In the method, a composition of the invention is applied to a site of interest. The method is effective for surgical sites, wounds, burns, and implantable devices.

In other aspects of the invention, devices for delivering the compositions of the invention are provided.

In one embodiment, the device includes (a) a first chamber comprising a crosslinkable polymer; and (b) a second chamber comprising multivalent metal ion and a hypohalite, wherein the multivalent metal ion is effective to crosslink the polymer. In one embodiment, the device further includes a removable barrier intermediate the first and second chambers. In another embodiment, the device further includes a third chamber adapted for receiving the polymer from the first chamber and for receiving the multivalent metal ion and hypohalite from the second chamber, wherein the third chamber further comprises an outlet for dispensing its contents. In a further embodiment, the device further includes a pump means in liquid communication with polymer in the first chamber and in liquid communication with the multivalent metal ion and hypohalite from the second chamber, wherein the pump means further comprises an outlet for dispensing the polymer, multivalent metal ion, and hypohalite.

In another embodiment, the device includes a substrate coated with a composition of the invention in dry form. Representative substrates include wound dressings and dental floss.

In a further aspect of the invention, the devices of the invention are used to deliver compositions of the invention. In one embodiment, viral, bacterial, parasitic, and fungal infections are treated by contacting a site of infection with a therapeutically effective amount of a composition delivered from a device of the invention. In another embodiment, a hypohalite is topically applied to a site of interest by applying a composition delivered from a device of the invention.

DESCRIPTION OF THE DRAWINGS

The foregoing aspects and many of the attendant advantages of this invention will become more readily appreciated and become better understood by reference to the following detailed description, when taken in conjunction with the accompanying drawings.

FIG. 1A illustrates the crosslinking by calcium ion with the alginate polymer resulting in the stable entrapment of the inactive form (hypohalite ion) within the polymeric matrix. The polymeric matrix viscosity and release rate can be varied by the length of the alginate, the ratio of calcium to alginate, the level of carboxylation of the alginate. FIG. 1B illustrates the conversion of coordinated hypochlorite to active forms hypochlorous acid and chlorine under acidic conditions and/or increase in temperature.

DETAILED DESCRIPTION OF THE INVENTION

The present invention provides compositions, systems, devices, and methods related to antimicrobial agents and their use to provide safe, effective, and sustained microbe killing while limiting toxicity to the host.

In one aspect of the invention, a composition is provided. In one embodiment, the composition includes a polymer crosslinked with a multivalent metal ion and having a hypohalite coordinated to the metal ion. In the composition, the polymer is non-covalently crosslinked by the metal ion as illustrated in FIG. 1A.

Suitable polymers include polymers that are capable of crosslinking with a multivalent metal ion. Representative polymers include biocompatible polymers. In certain embodiments, the polymer is a gel forming polymer and the resultant crosslinked polymer is a hydrogel. As used herein, the term "crosslinked polymer" refers to polymers that are intramolecularly crosslinked (i.e., crosslinks within a polymer) and polymers that are intermolecularly crosslinked (i.e., crosslinks between polymers). To facilitate multivalent metal ion crosslinking, the crosslinkable polymer include one or more functional groups effective to coordinate the metal ion and crosslink the polymer. Representative functional groups include carboxylic acid groups. In one embodiment, the polymer is a carboxylic acid-containing polymer. For example, poly(N-isopropylacrylamide)-carboxylic acid terminated (NIPAM-COO⁻) (molecular weight up to about 10,000), carboxymethycellulose, carboxycellulose, and caboxylated dextran, which exhibit multivalent negative charged polymers are suitable for crosslinking by calcium hypohalite.

Suitable polymers include biological polymers derived from biological monomers. Suitable polymers include polysaccharides derived from sugars, polyamino acids derived from amino acids, and polynucleic acids derived from nucleic acids. Representative polysaccharides include celluloses and alginates. Representative polyamino acids include polyarginines. Representative polynucleic acids include DNAs, RNAs, and aptamers. These polymers can be formed from monomers that include functional groups suitable for metal ion crosslinking or modified as polymers to include functional groups suitable for metal ion crosslinking.

In one embodiment, the polymer is an alginate. In another embodiment, the polymer is a carboxylalkylcellulose (e.g., carboxymethylcellulose, carboxyethylcellulose).

The polymer is present in the composition in an amount from about 0.1 to about 40 percent by weight based on the total weight of the composition. In one embodiment, the polymer is present in the composition in an amount from about 1 to about 25 percent by weight based on the total weight of the composition. In another embodiment, the polymer is present in the composition in an amount from about 1 to about 20 percent by weight based on the total weight of the composition. In another embodiment, the polymer is present in the composition in an amount from about 5 to about 25 percent by weight based on the total weight of the composition. In a further embodiment, the polymer is present in the composition in an amount from about 15 to about 20 percent by weight based on the total weight of the composition.

The composition of the invention includes a multivalent metal ion. Suitable multivalent metal ions are effective to crosslink the composition's crosslinkable polymer. As used herein, the term "multivalent metal ion" refers to divalent metal ions, trivalent metal ions, and mixtures thereof. Suitable multivalent metal ions include alkaline earth metal ions, transition metal ions, and Group III metals ions. Representative divalent metal ions include magnesium, calcium, strontium, and barium ions. Representative transition metal ions include scandium, copper, zinc, tin, iron, titanium, and manganese ions. Representative trivalent metal ions include aluminum, gallium, indium, and thallium ions. The multivalent metal ion is present in the composition in an amount from about 1 to about 25 percent by weight based on the total weight of the composition. In another embodiment, the multivalent metal ion is present in the composition in an amount from about 1 to about 20 percent by weight based on the total weight of the composition.

The active agent generated by the composition of the invention is derived from the coordinated hypohalite. Representative hypohalites useful in the composition include hypofluorite, hypochlorite, hypobromite, and hypoiodite, and mixtures thereof. In one embodiment, the hypohalite is present in the composition in an amount from about 0.1 to about 40 percent by weight based on the total weight of the composition. In another embodiment, the hypohalite is present in the composition in an amount from about 1 to about 25 percent by weight based on the total weight of the composition. In another embodiment, the hypohalite is present in the composition in an amount from about 1 to about 20 percent by weight based on the total weight of the composition. In another embodiment, the hypohalite is present in the composition in an amount from about 5 to about 25 percent by weight based on the total weight of the composition. In a further embodiment, the hypohalite is present in the composition in an amount from about 15 to about 20 percent by weight based on the total weight of the composition.

The composition of the invention can take a variety of forms depending on the desired method for its use. In one embodiment, the composition is a hydrogel. In another embodiment, the composition is a dry powder. In a further embodiment, the composition is a liquid solution. In another embodiment, the composition is in the form of a microencapsulated particle.

The sustaining and penetrating antimicrobial halogen composition described herein provides adequate concentrations of active agent for killing microbes or fungi on contact. On contact with a site of interest, the composition provides an active agent that is released upon a change in temperature and/or pH, over time.

Figure 1:
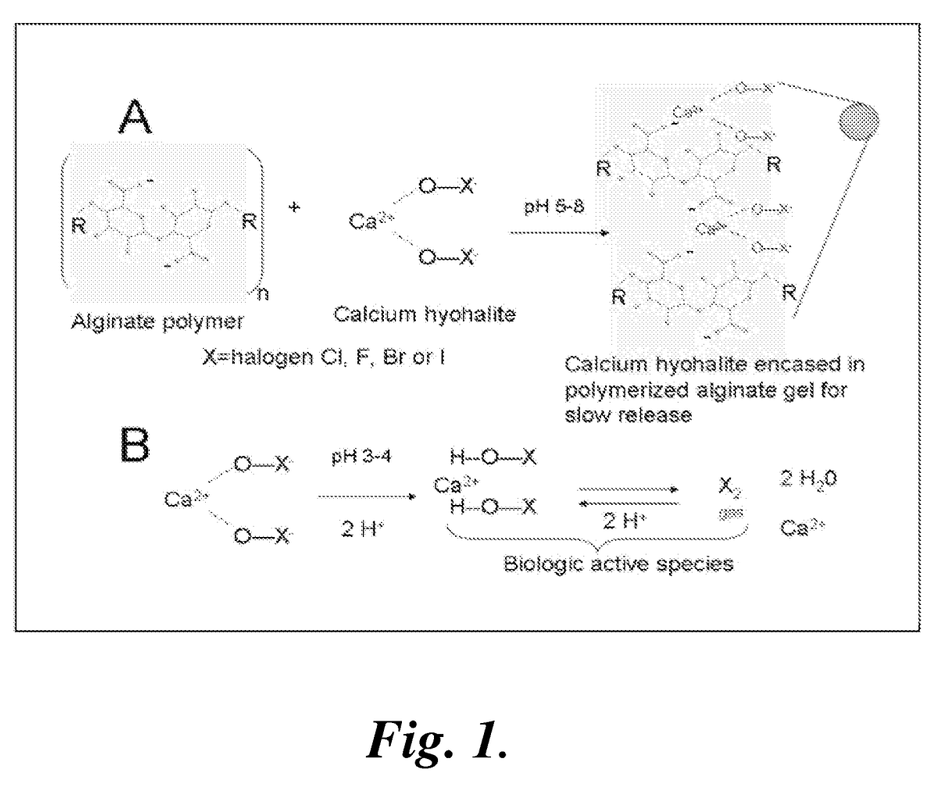
FIGS. 1A and 1B present a diagrammatic view of a representative antimicrobial system of the invention for sustained release of a halogen.

In certain embodiments, the invention provides an antimicrobial composition including a liquid hypochlorite and one or more active acidic forms of hypochlorous acid and chlorine gas. Hypochlorous acid and chlorine gas are in an equilibrium that is controlled by one or more of multivalent metal ion (e.g., calcium ion), temperature, and pH. At storage conditions, calcium hypochlorite solubility is limited under high pH. The hypochlorite ion is encased in a polymeric matrix that is formed via a calcium ion mediated process. The matrix viscosity and permeability control the availability of hypochlorite for generation of hypochlorous acid and chlorine gas. Upon application at an affected area, a reduction in pH or increase in temperature trigger the release and conversion of hypochlorite to the active acidic forms (hypochlorous acid and chlorine gas), resulting in maximally providing long-acting antimicrobial and/or antifungal activities. This concept is illustrated in FIG. 1.

In certain embodiments, the composition includes a polymeric alginate that forms an ionic hydrogel-like polymer upon crosslinking with a divalent positive ion such as calcium. Depending on the length of the ionic polymer and their final concentrations, gel-like property may or may not present; but the polymer crosslinked with the active calcium hypochlorite would provide similar release of hypochlorite for generation of hypochlorous acid and chlorine gas. In these embodiments, alginate can be present in the composition from about 1 to about 15 percent by weight.

Figure 2:
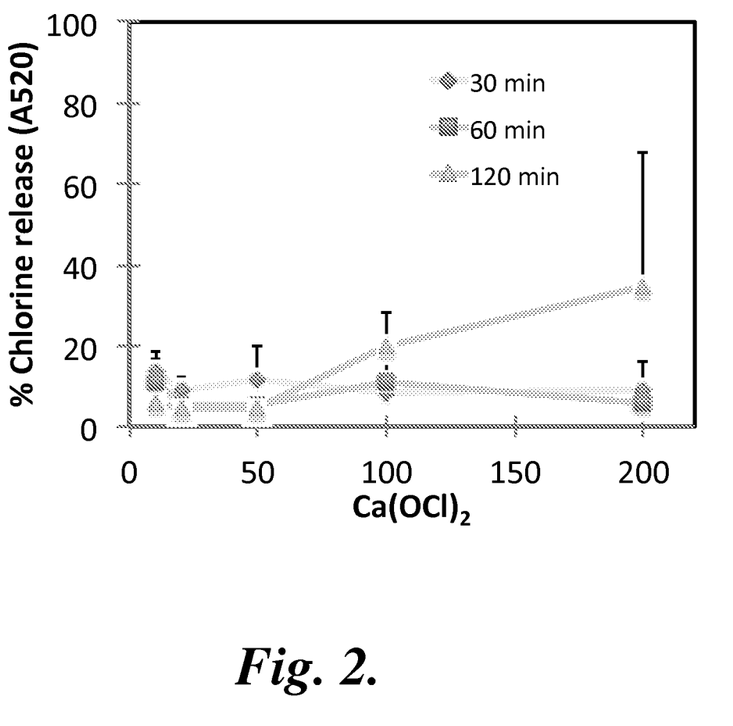
FIG. 2 illustrates the release of chlorine over time for a representative alginate calcium hypochlorite composition of the invention. The release of chlorine was determined by absorbance measurement at 520 nm using N,N-diethyl-p-phenylenediamine (DPD). The replicated data is presented as a mean±standard deviation percentage release.

In one embodiment, the interactions of calcium hypochlorite and alginate control the release of chlorine over time, which allows prolonged and continuous exposure. Without stabilization of calcium hypochlorite in alginate-calcium hydrogel, calcium hypochlorite at a concentration of 200 mg/ml is decomposed under ambient light within 30 min at 37° C. In a composition containing 1% alginate tested at room temperature (without exposing to light), about 40-50% of chlorine was released over 2 hr test period for all calcium hypochlorite concentrations tested (FIG. 2). Although FIG. 2 shows a single % of alginate for conceptual illustration, it is understood that a range of alginate concentration and polymer size may be employed such as 1-15%. It is understood that the physical structure of the gel can take the form of particles, sheets, or appropriate structure to optimize the surface suitable for release of the active hypohalite form.

Figure 3:
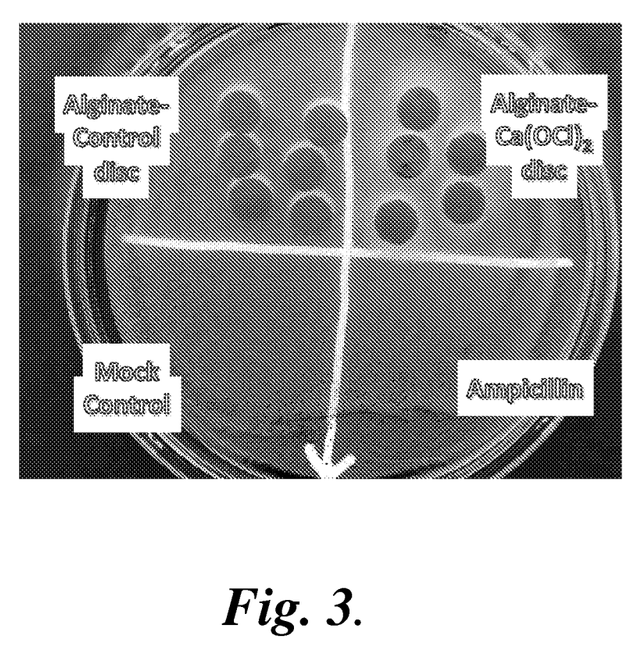
FIG. 3 is an image of an agar plate seeded with E. coli comparing antimicrobial activity of a representative alginate calcium hypochlorite composition of the invention in a coated disc system. Upper right quadrant: alginate calcium hypochlorite hydrogel coated discs. Upper left quadrant: alginate coated discs. Lower left: buffer only. Lower right: ampicillan as a positive control. Note clearing around alginate calcium hypochlorite hydrogel coated discs in upper right.

A cellulose matrix was used to demonstrate antimicrobial activity of an alginate-calcium hypochlorite hydrogel. Using *E. coli* grown in an agar plate, the circular disc was coated with alginate-calcium hypochlorite hydrogel and the bacteria allowed to grow for 24 hrs. FIG. 3 illustrates the antimicrobial function of alginate-calcium hypochlorite hydrogel coated on a cellulose support. The antimicrobial activity was sustained over the 24 hr test period; the control alginate without calcium hypochlorite (active crosslinker and hypochlorous acid) did not exhibit antimicrobial activity.

In accordance with the various embodiments, a suitable configuration may include a mixture of calcium hypochlorite and water or other aqueous solutions as solvents. The fraction of each solvent and alginate solution may vary, but it may generally contain approximately 1-5% alginate, 1-2% calcium hypochlorite, and 40-80% water (and other pharmaceutically acceptable excipients). In addition, the antimicrobial system may be formulated to include various ionic and non-ionic antimicrobial agents, and may also include zwitterions containing quaternary ammonium centers, which has demonstrated the required for antimicrobial activity when applied to a device that exhibits surface contamination while also generating a liquid or semi-solid polymer coating for release of the active antimicrobial agent for a range of 1 to 24 hours. In various additional embodiments, the release of the antimicrobial agent may be from about 1 to 18 hours, about 1 to 14 hours, about 1 to 12 hours, about 1 to 10 hours, about 1 to 6 hours, about 1 to 3 hours, or about 1 to 2 hours. Furthermore, the system and embodiments described herein provides advantages of controlling, preventing, and/or minimizing evaporation from the surface within approximately 2 to 24 hr after application.

While the foregoing polymeric formulation may provide suitable antimicrobial action, with adequate surface wetting properties and evaporation rates following application, the antimicrobial solution may also include various other compounds and excipients.

In accordance with the various embodiments, a suitable configuration may include a combination of more than one halogen species in the antimicrobial system. By way of example, a combination of chlorine and bromine has been demonstrated to be more effective. In environmental studies testing the combination as a disinfectant, even resistance microbes are eliminated faster and with higher potency than achieved with chlorine or bromine alone. One exemplary concentration range of chlorine and bromine includes 0.5-5 ppm or 06-6 mg/mL chlorine:bromine (9:1) combination. In one exemplary embodiment, an antimicrobial effective concentration achieved with the present disclosed system using 200 mg/ml calcium hypohalite is at least 30 fold higher than the concentration required for anti-microbial effects. Although the chlorine and bromine combination is presented for illustration purpose, it is understood that other combinations of halogens and antimicrobial agents could be used to increase potency and overcome drug resistance as well as provide broader antimicrobial coverage. It is also understood further that the halogen or other substances may be in ionic form or presented with counter ion other than calcium.

In another aspect of the invention, devices that deliver the composition of the invention are provided. The compositions of the invention are advantageously delivered to a site of interest to be treated (e.g., site of viral, bacterial, or fungal infection or parasitic infestation) by a device of the invention. In general, the devices store the composition's precursors (i.e., crosslinkable polymer and multivalent metal ion/hypochlorite) separately and provide for their combination and ultimate composition formation either in situ immediately prior to or at the time of delivery to the site of interest.

The device includes a first chamber comprising a crosslinkable polymer, and a second chamber comprising multivalent metal ion and a hypohalite. The multivalent metal ion is effective to crosslink the polymer. The first and/or second chambers may further include an aqueous medium (e.g., an aqueous buffer).

Figure 4:
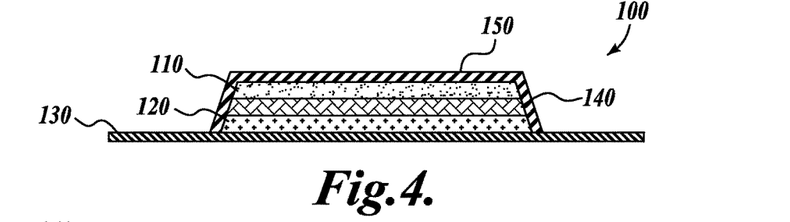
FIG. 4 is a schematic illustration of a first representative device of the invention useful for delivering a composition of the invention.

In one embodiment, the device includes a removable barrier intermediate the first and second chambers. In this embodiment, the device is an appliance such as a dressing or bandage. FIG. 4 is a schematic illustration of a representative appliance of the invention effective for delivering a composition of the invention. Referring to FIG. 4, appliance 100 includes housing 150 enclosing first and second chambers 110 and 120, respectively. One chamber contains crosslinkable polymer and the other contains multivalent metal ion and hypohalite. Chambers 110 and 120 are separated by removable barrier 140. Appliance 100 also includes substrate 130 for adhering the appliance to the site of interest. To assist in effectiveness, housing 150 may be or include a gas impermeable membrane to direct activate agent flow toward the site of interest. Appliance 100 can be adhered to the site of interest and, once the barrier is removed and the contents of the first and second chamber begin mixing, provide sustained release of active agent to the site of interest.

The barrier can be a membrane that includes a release mechanism configured to enable a user to remove the barrier thereby enabling a mixing of the polymer and the multivalent metal ion/hypohalite. The release mechanism may be embodied in a tab formed as part of the barrier. The tab can extend to the exterior of the appliance thereby allowing a user to pull the tab, thereby removing the barrier.

It is contemplated that the appliance may include a liquid layer having a solution configured to be a wetting agent, control pH of the polymer/multivalent ion/hypohalite mixture, or control or enhance the flow of the materials. Furthermore, the liquid layer may assist in facilitating the flow of the composition mixture through porous sections of an adhesive release liner. It is contemplated that the liquid layer may be separate from the gel polymer and multivalent ion/hypochlorite. Additionally, it is contemplated that the liquid layer may be incorporated as part of the polymer composition. By way of example, the polymer may be formulated to include a wetting agent or pH controller (such as a buffering agent).

The appliance can further include a gas retaining, or gas impermeable membrane that, together with the adhesive release liner, encase or substantially encase the internal structure of the appliance.

Figures 5, 6, 7:
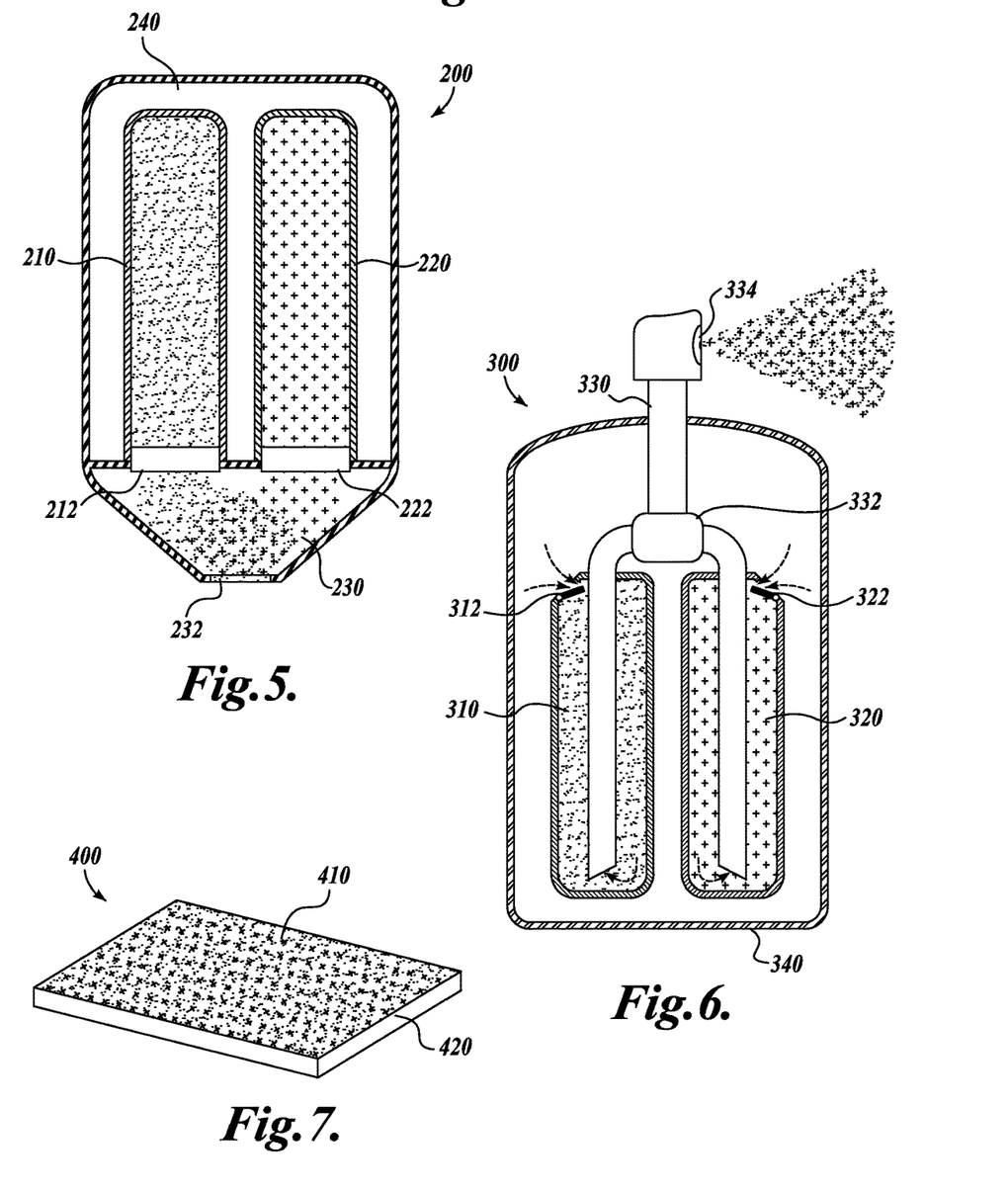
FIG. 5 is a schematic illustration of a second representative device of the invention useful for delivering a composition of the invention.
FIG. 6 is a schematic illustration of a third representative device of the invention useful for delivering a composition of the invention.
FIG. 7 is a schematic illustration of a fourth representative device of the invention useful for delivering a composition of the invention.
Figure 8A:
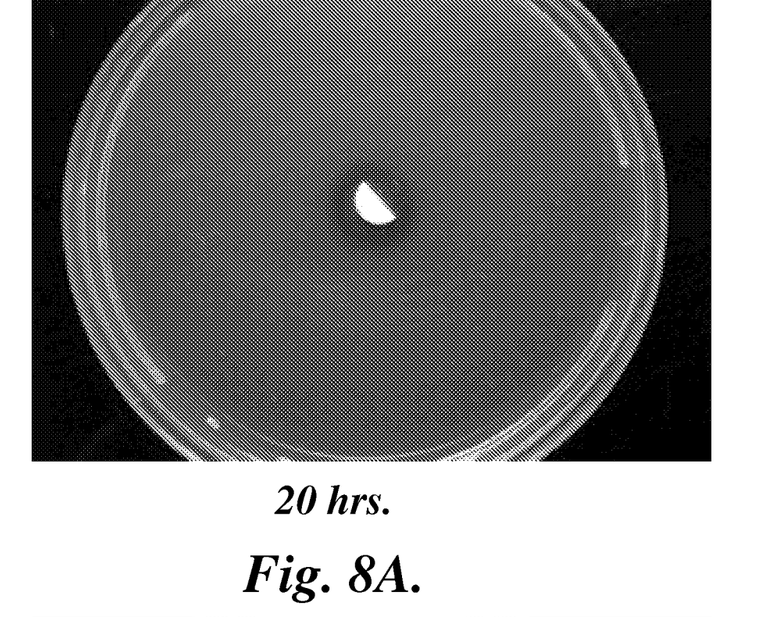
FIGS. 8A-8D are images of agar plates seeded with XL1-Blue colonies cultured overnight (1/10 dilution, $OD_{570 \, nm}$=0.167, fresh culture) comparing nail penetration for a representative alginate calcium chlorite composition of the invention. Application [10 µl calcium chlorite 200 mg/ml+ 1% sodium alginate (1:1 v/v)] to a filter disk (d=5 mm) (8A and 8C) and direct application to nail under filter disk (8B and 8D). Kill compared at 20 hr (8A and 8B) and at 92 hr (8C and 8D). 100% kill was observed in both instances.
Figure 8B:
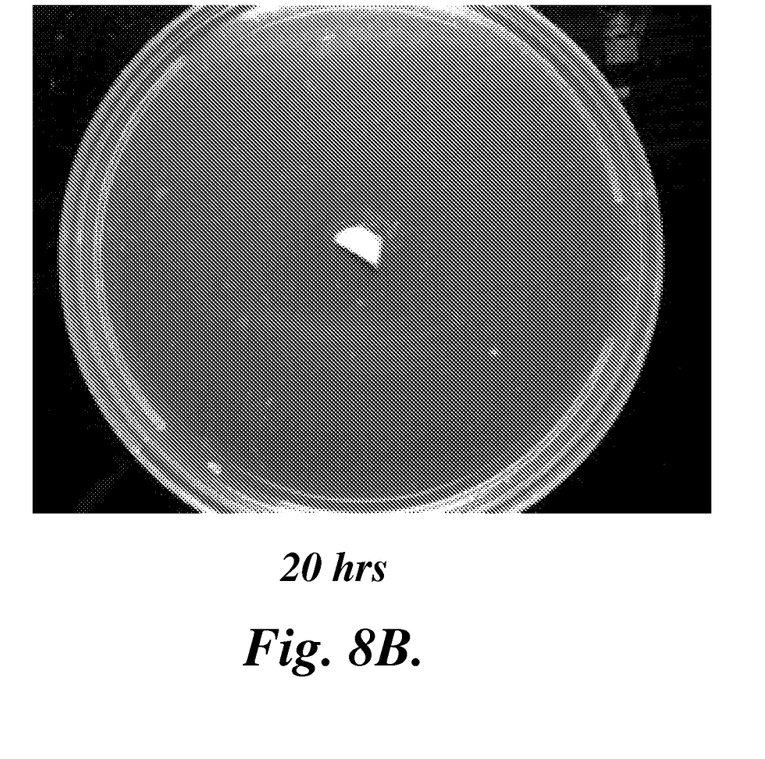
Figure 8C:
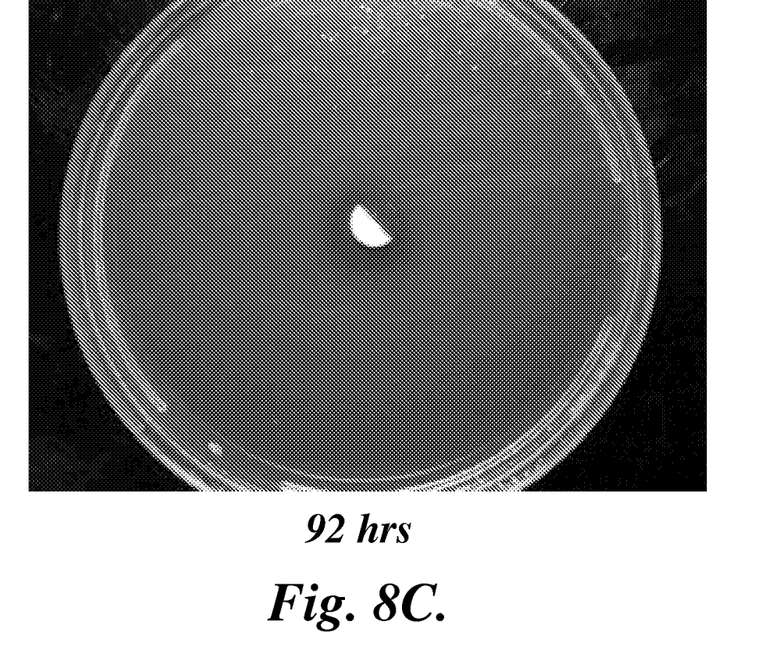
Figure 8D:
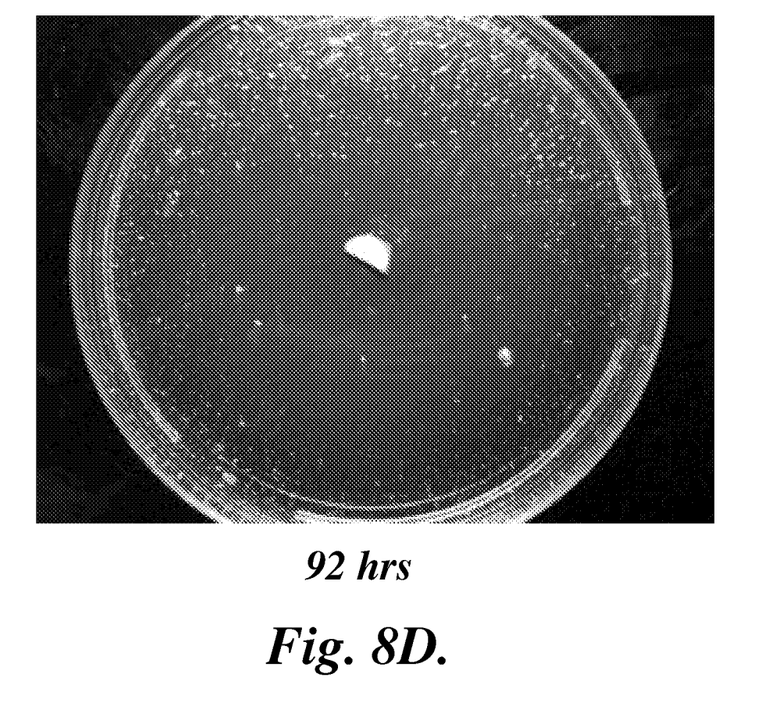
Figure 9A:
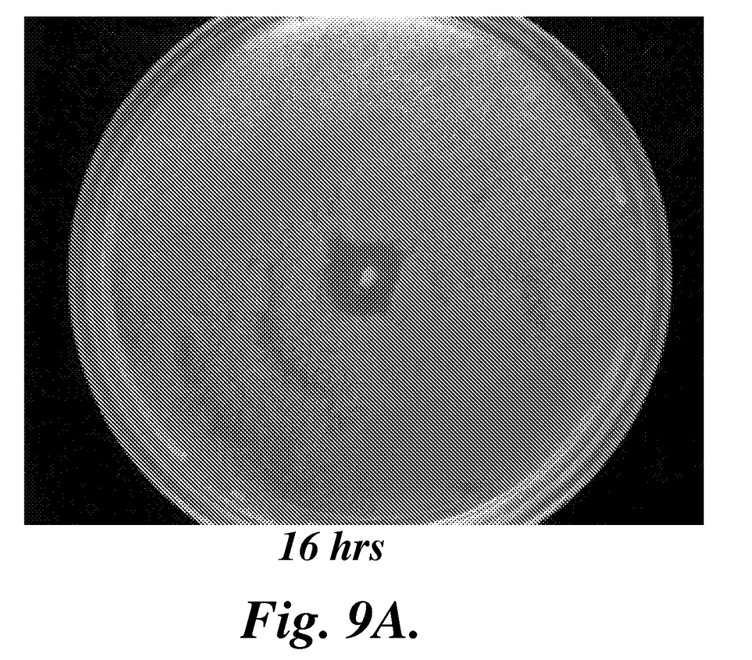
FIGS. 9A and 9B are images of agar plates seed with XL1-Blue colonies cultured for overnight ($OD_{570}$ nm=0.164, fresh lawn) comparing effectiveness of a nail soaked in calcium hypochlorite 200 mg/ml and 1% sodium alginate (SA) overnight at 4° C. Images were taken at 16 hr (9A) and 40 hr (9B).
Figure 9B:
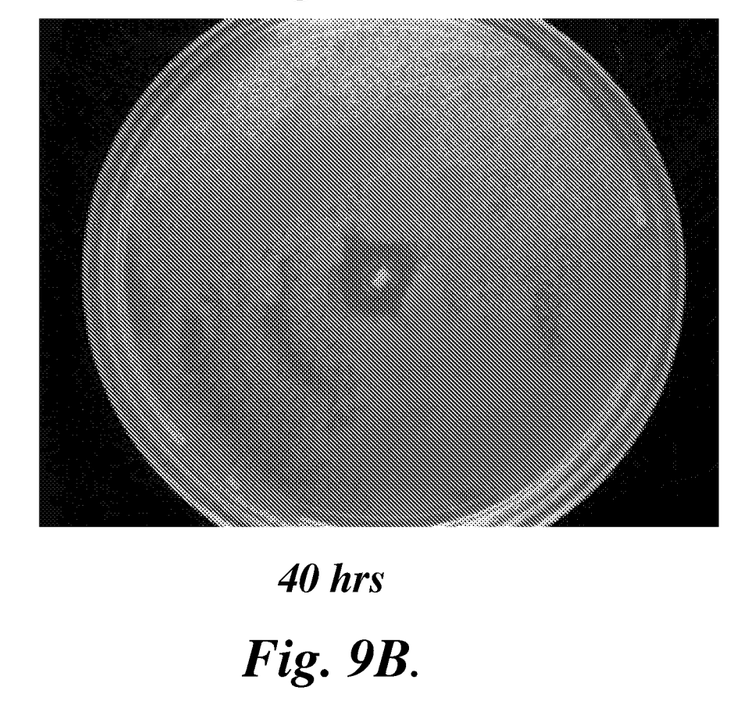
Figure 10A:
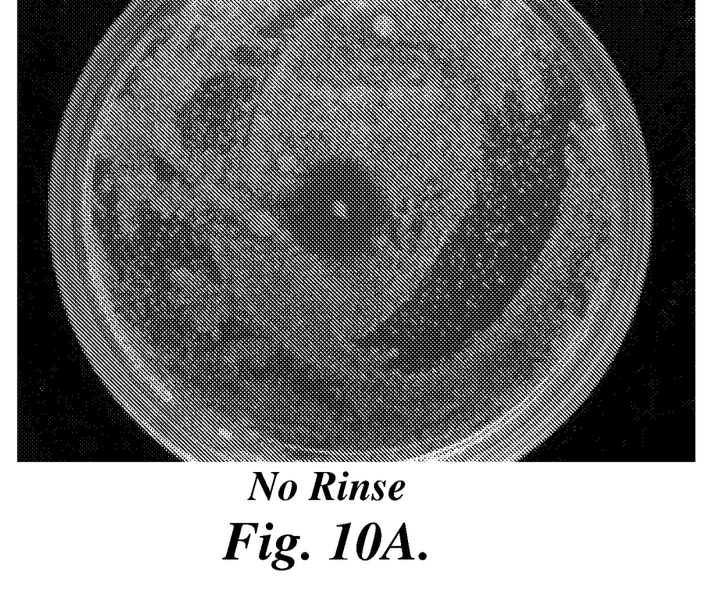
FIGS. 10A-10D are images of agar plates seeded with XL1-Blue colonies cultured for 4 hr ($OD_{570 \, nm}$=0.084) comparing effectiveness of a rinse on nail penetration. Calcium hypochlorite 200 mg/ml and 1% sodium alginate (1:1) on nail, 4 hr at 4° C.: no rinse (10A) and rinse (10B). Bleach—sodium hypochlorite controls (10C): 0, water; 1, 5 mg/ml; 2, 20 mg/ml; and 3, 60 mg/ml. Gentamicin controls (10D): 0, water; 1, 1×; 2, 10×, and 3, 100×. Results indicate no clear effects on killing with antimicrobial agent pre-soaked nail.
Figure 10B:
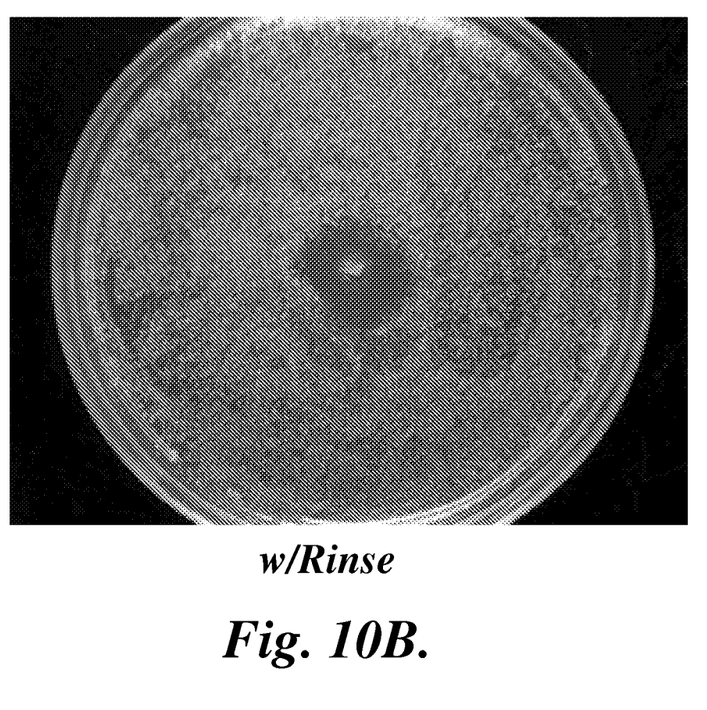
Figure 10C:
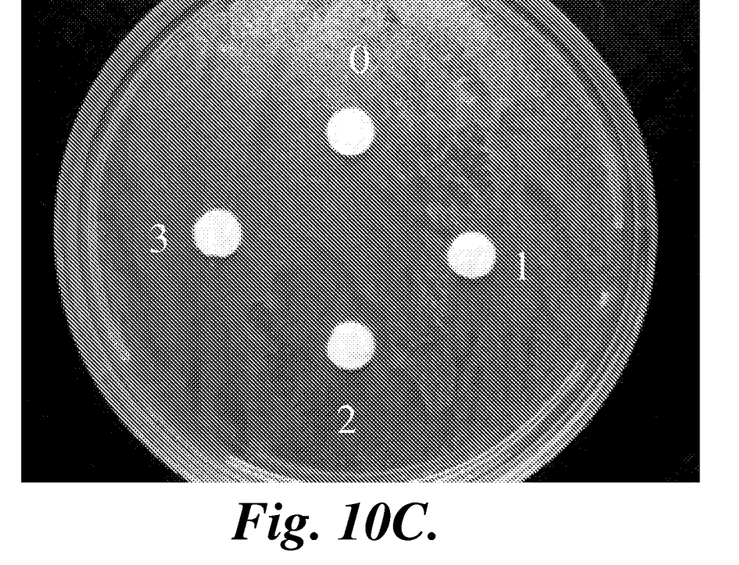
Figure 10D:
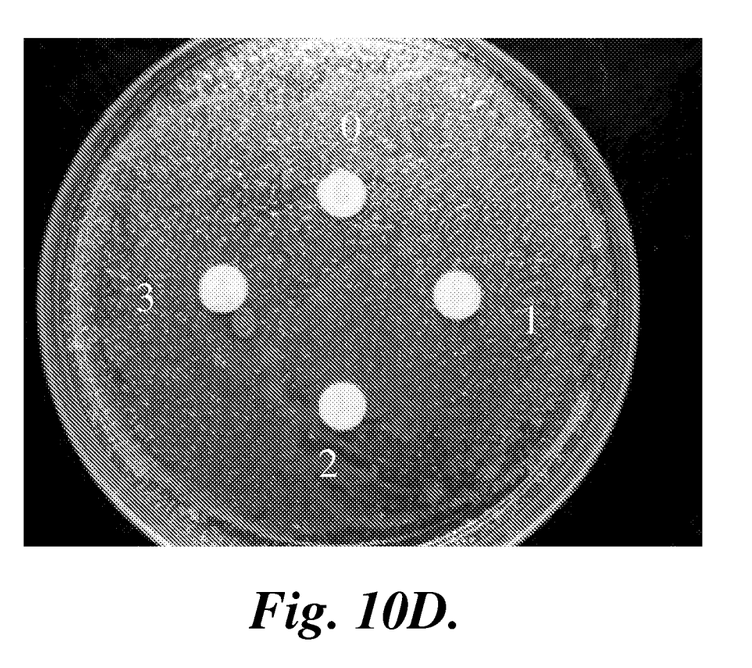
Figure 11A:
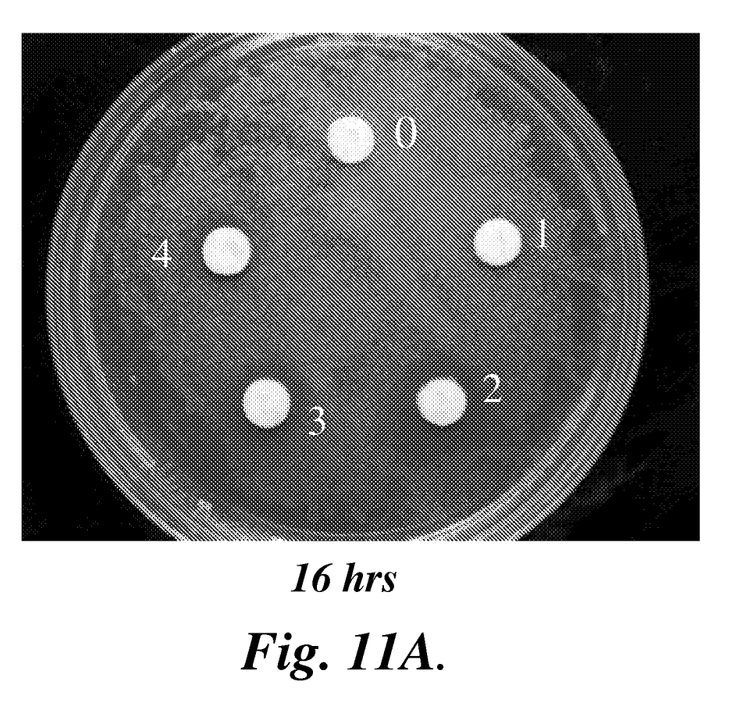
FIGS. 11A-11D are images of agar plates seeded with XL-1 antibiotic resistant bacteria comparing the effectiveness of sodium hypochlorite (11A and 11C) and calcium hypochlorite (11B and 11D) at 16 hr (11A and 11B) and 40 hr (11C and 11D). Sodium hypochlorite (11A and 11C): 0, water; 1 30 mg/ml with alginate; 2, 60 mg/ml with alginate; 3, 60 mg/ml without alginate; 4, 30 mg/ml without alginate. Calcium hypochlorite (11B and 11D): 0, water; 1 25 mg/ml with alginate; 2, 50 mg/ml with alginate; 3, 50 mg/ml without alginate; 4, 25 mg/ml without alginate. The results indicate that sodium chlorite effectiveness is not affected by the presence of alginate.
Figure 11B:
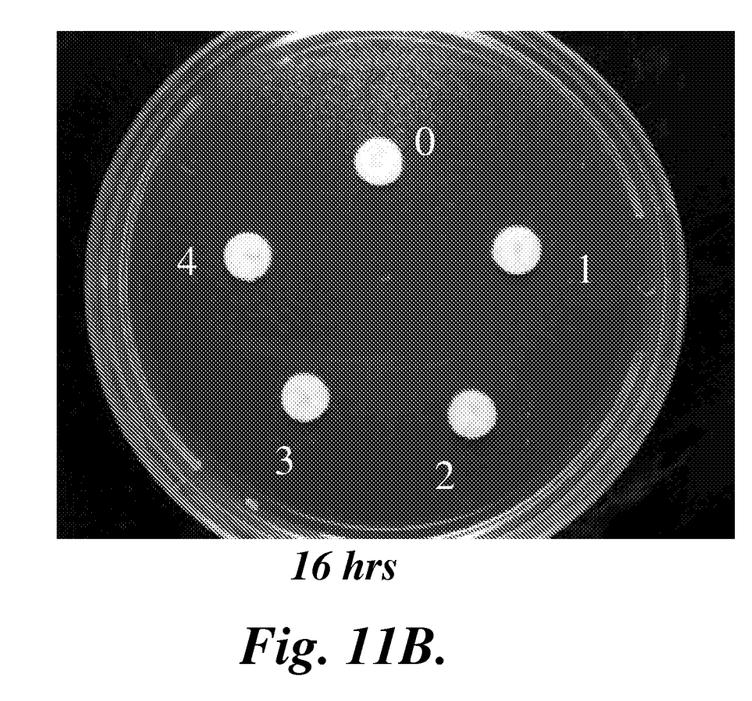
Figure 11C:
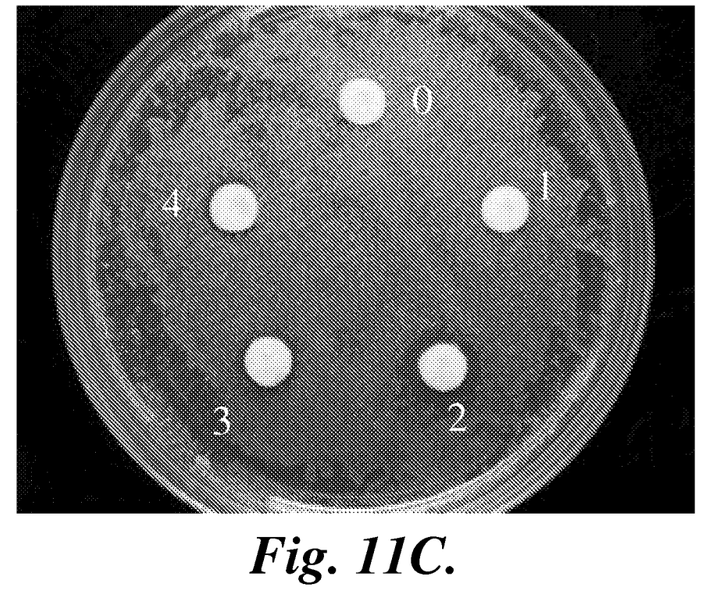
Figure 11D:
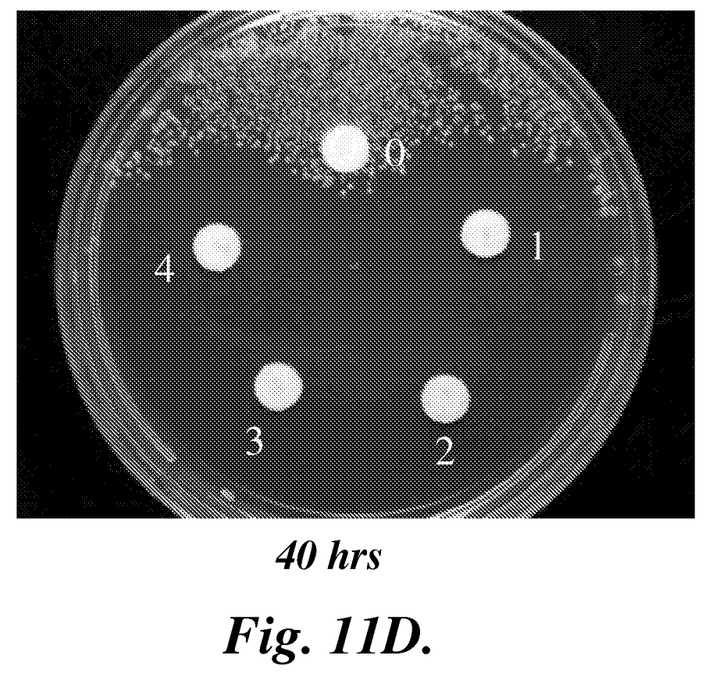
Figure 12A:
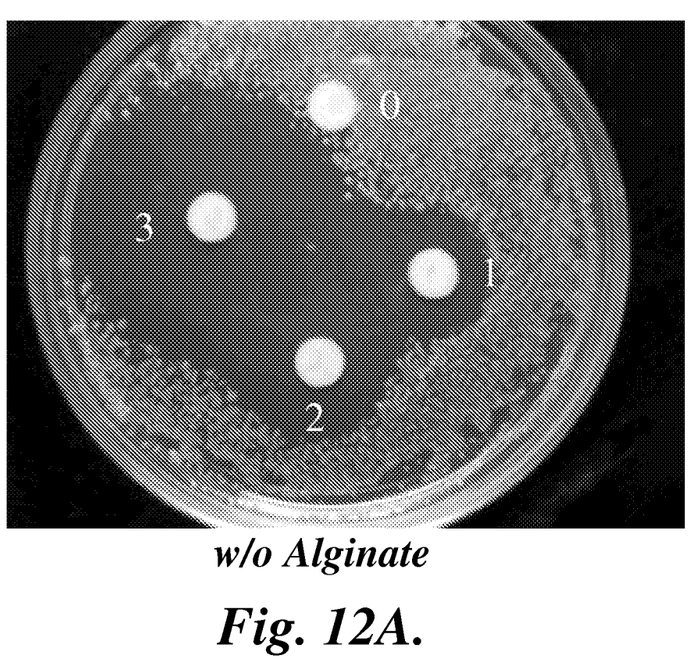
FIGS. 12A and 12B are images of agar plates seeded with XL1-Blue colonies cultured overnight ($OD_{570 \, nm}$=0.164, fresh lawn) comparing the effectiveness of calcium hypochlorite without alginate (12A) and with alginate (12B) at 40-48 hr: 0, water; 1, 10 mg/ml calcium hypochlorite; 2, 20 mg/ml calcium hypochlorite; 3, 50 mg/ml calcium hypochlorite. The results indicate that alginate is effective for sustained antimicrobial effects.
Figure 12B:
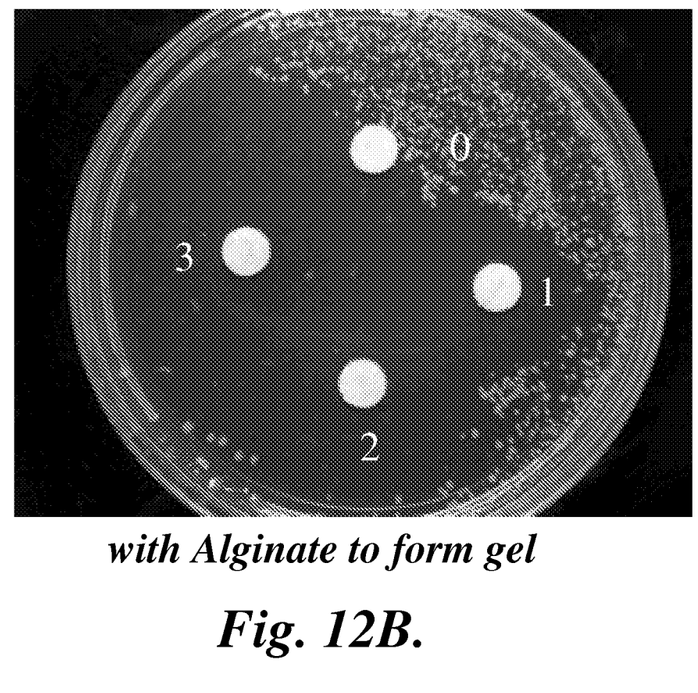
Figure 13:
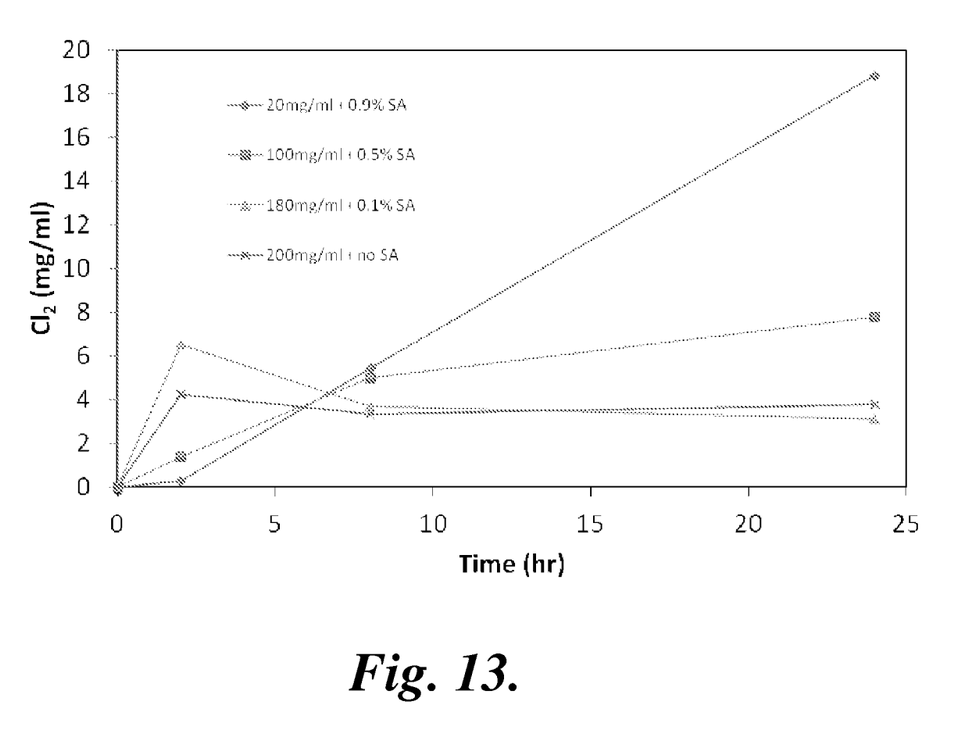
FIG. 13 is a graph comparing chlorine release as a function of time demonstrating the effect of calcium-alginate ratio on chlorine release from a calcium hypochlorite coated nail (dose normalized to 200 mg/ml): 20 mg/ml calcium hypochlorite and 0.9% sodium alginate; 100 mg/ml calcium hypochlorite and 0.5% sodium alginate; 180 mg/ml calcium hypochlorite and 0.1% sodium alginate; and 200 mg/ml calcium hypochlorite and no sodium alginate. The results indicate the effectiveness of increased sodium alginate in the composition.

In another embodiment, the device of the invention further includes a third chamber adapted for receiving the polymer from the first chamber and for receiving the multivalent metal ion and hypohalite from the second chamber. The third chamber further includes an outlet for dispensing its contents. In this embodiment, the device is an applicator device. FIG. 5 is a schematic illustration of a representative applicator device of the invention useful for delivering a composition of the invention. Referring to FIG. 5, applicator 200 includes housing 240 enclosing first and second chambers 210 and 220, respectively. One chamber contains crosslinkable polymer and the other contains multivalent metal ion and hypohalite. Chambers 210 and 220 are separated from third chamber 230 by pressure-sensitive check and release valves 212 and 222, respectively. Upon application of pressure to the first and second chambers (e.g., applying pressure to housing 240), at least a portion of the contents of the first and second chambers are conducted to the third chamber where mixing occurs to provide active agent. The mixture containing active agent exits the applicator through outlet 232. Applicator 200 is effective for applying active agent to the site of interest.

In a further embodiment, the device of the invention further includes a pump means in liquid communication with polymer in the first chamber and in liquid communication with the multivalent metal ion and hypohalite in the second chamber. The pump means further includes an outlet for dispensing the polymer, multivalent metal ion, and hypohalite. In this embodiment, the device is a spray or aerosol dispensing device. FIG. 6 is a schematic illustration of a representative spray or aerosol device of the invention useful for delivering a composition of the invention. Referring to FIG. 6, device 300 includes housing 340 enclosing first and second chambers 310 and 320, respectively. One chamber contains crosslinkable polymer and the other contains multivalent metal ion and hypohalite. Chambers 310 and 320 are in liquid communication through pump means 330. Chambers 310 and 320 can be pressurized through one-way check valves 312 and 322, respectively, thereby introducing the contents of the first and second chambers into the pump means through mixing and metering valve 332. The combined contents of the first and second chambers are exited from the device through outlet 334. Spray device 300 is effective for applying active agent to the site of interest.

In yet another embodiment, the device of the invention is a substrate having at least a portion of the substrate coated with a composition of the invention in dry form. In this embodiment, the device relies on wetting from the environment of the site of interest to activate the composition. FIG. 7 is a schematic illustration of a representative coated substrate device of the invention useful for delivering a composition of the invention. Referring to FIG. 7, device 400 includes substrate 420 on which the composition of the invention 410 resides in dry form. Once wetted, the composition in dry form becomes activated to provide active agent. The substrate bearing the composition of the invention in dry form can be contacted with the site of interest and become activated by the contact (wetting). The substrate is effective for applying active agent to the site of interest. Representative substrates include wound dressings (e.g., gauze) and dental floss.

Dry powder forms of the composition can be activated by the application of an aqueous solution that is administered via a spray bottle, syringe, or by soaking in aqueous solution prior to its use.

In a further aspect, the invention provides methods for topical application of a hypohalite. In one embodiment, the method includes applying a composition of the invention to a site of interest. Application of a composition of the invention to a site of interest advantageously delivers active agent to the site. Representative sites of interest include surgical sites (i.e., pre- and post-surgery sites), wounds sites, ulcers sites, and burn sites. Other sites of interest that benefit from application of the composition of the invention include implantable devices such as artificial joints and catheters. In the methods, the hypohalite can be applied by spraying, washing, or rinsing. Exemplary uses include oral and vaginal rinse, oral lozenge or vaginal suppository, dental applications for treatment of teeth and gums and oral surgery sites.

Topical application of the hypohalite can be achieved using the devices of the invention to deliver the composition to a site of interest.

In a further aspect of the invention, methods for treating infections are provided. In certain embodiments, the invention provides a method for treating a viral, bacterial, fungal infection, parasitic infection in an animal (e.g., human subject). In the method, a site of infection or infestation is contacted with a therapeutically effective amount of a composition of the invention. The composition of the invention is effective in treating infections caused by pathogenic microbes affecting skin and associated appendages (e.g., nail, hair follicle, sebaceous gland). The composition is effective for treating infections of keratin and tissues surrounding keratinous structure. The composition is also effective for treating infections of the mucosa including oral and genital skin. The therapeutic advantages of the composition result from penetration of hypochlorite into and through skin, mucosa, and skin appendages.

In one embodiment, the infection is a fungal infection. Representative fungal infections treatable by the composition of the invention include onychomycosis.

In the methods, the therapeutically effective amount of the composition of the invention can be delivered from a device of the invention.

It is contemplated that the composition described herein can be used to prevent or treat a variety of other superficial microbial infections, including athlete's foot, cellulitis, chronic ulcers, and secondary infection due to burns. Infections with specific organisms that could be treated include viruses such influenza, norovirus, rotaviruses; bacteria such as *Pseudomonas, Clostridium difficile, E. coli*, and methicillin resistant staphyloccous; and fungi such as *Aspergillus*, yeast (e.g., *Candida albicans*), and mucor. The composition is also useful in the treatment of biofilms in chronic wounds, dentistry, and on hardware used in surgery and for implants.

While illustrative embodiments have been illustrated and described, it will be appreciated that various changes can be made therein without departing from the spirit and scope of the invention.

The embodiments of the invention in which an exclusive property or privilege is claimed are defined as follows:

1. A composition which releases a halogen topically to skin or skin appendages, comprising a polymer crosslinked with calcium ions, wherein the calcium ion comprises between about 1.5 to 25 percent by weight of the composition, and a hypochlorite coordinated to the calcium ion, wherein the rate of release of the chlorine is between about 1% per hour to about 20% per hour, wherein said rate of release is regulated at least by the ratio of said calcium ion to said polymer, and wherein the composition is in the form of a hydrogel or a liquid solution.

2. The composition of claim 1, wherein the polymer is a carboxylic acid-containing polymer.

3. The composition of claim 1, wherein the polymer is selected from the group consisting of a polysaccharide, a poly(amino acid), and a poly(nucleic acid).

4. The composition of claim 1, wherein the polymer is selected from the group consisting of alginates and carboxylalkylcelluloses.

5. A method for treating a viral, bacterial, fungal, or parasitic infection in an animal, comprising contacting a site of infection with a therapeutically effective amount of a composition of claim 1.

6. The method of claim 5, wherein the infection is a fungal infection.

7. The method of claim 5, wherein the site of infection is the skin or skin appendage, mucosa, or human nail.

8. A method for topical application of hypochlorite, comprising applying a composition of claim 1 to a site of interest.

9. The method of claim 8, wherein the site of interest is a surgical site, a wound, a burn, or an implantable.

10. A device, comprising a substrate coated with a composition of claim 1.

11. A method for treating a viral, bacterial, parasitic, or fungal infection in an animal, comprising contacting a site of infection with a therapeutically effective amount of a composition delivered from a device of claim 10.

12. A method for topical application of hypochlorite, comprising applying a composition delivered from a device of claim 10 to a site of interest.

* * * * *